(12) United States Patent
Perkins et al.

(10) Patent No.: US 8,136,526 B2
(45) Date of Patent: Mar. 20, 2012

(54) METHODS AND DEVICES TO INDUCE CONTROLLED ATELECTASIS AND HYPOXIC PULMONARY VASOCONSTRICTION

(75) Inventors: Rodney C. Perkins, Woodside, CA (US); Nikolai Aljuri, Revere, MA (US); Ajit Nair, Milpitas, CA (US)

(73) Assignee: Pulmonx Corporation, Redwood City, CA (US)

( * ) Notice: Subject to any disclaimer, the term of this patent is extended or adjusted under 35 U.S.C. 154(b) by 783 days.

(21) Appl. No.: 11/682,986

(22) Filed: Mar. 7, 2007

(65) Prior Publication Data

US 2007/0225747 A1    Sep. 27, 2007

Related U.S. Application Data

(60) Provisional application No. 60/780,577, filed on Mar. 8, 2006.

(51) Int. Cl.
*A61M 16/00* (2006.01)

(52) U.S. Cl. ......... 128/207.15; 128/200.24; 128/207.14; 128/207.16; 128/899

(58) Field of Classification Search ............. 128/207.15, 128/200.24, 207.16, 899; 623/23.68, 23.65, 623/23.7, 1.15, 1.24, 1.14, 1.35
See application file for complete search history.

(56) References Cited

U.S. PATENT DOCUMENTS

| | | | |
|---|---|---|---|
| 6,527,761 B1 | 3/2003 | Soltesz et al. | |
| 6,679,264 B1 | 1/2004 | Deem et al. | |
| 6,722,360 B2 | 4/2004 | Doshi | |
| 6,941,950 B2 | 9/2005 | Wilson et al. | |
| 7,011,094 B2 | 3/2006 | Rapacki et al. | |
| 7,276,077 B2 | 10/2007 | Zadno-Azizi et al. | |
| 7,412,977 B2 * | 8/2008 | Fields et al. | 128/200.24 |
| 7,434,578 B2 * | 10/2008 | Dillard et al. | 128/200.24 |
| 7,533,671 B2 * | 5/2009 | Gonzalez et al. | 128/207.12 |
| 7,549,984 B2 * | 6/2009 | Mathis | 604/509 |
| 2001/0037808 A1 | 11/2001 | Deem et al. | |
| 2003/0127090 A1 * | 7/2003 | Gifford et al. | 128/200.24 |
| 2004/0060563 A1 * | 4/2004 | Rapacki et al. | 128/207.14 |
| 2004/0073191 A1 | 4/2004 | Soltesz et al. | |
| 2004/0210298 A1 * | 10/2004 | Rabkin et al. | 623/1.11 |
| 2005/0196344 A1 | 9/2005 | McCutcheon et al. | |
| 2006/0102186 A1 | 5/2006 | Adler | |
| 2006/0135947 A1 | 6/2006 | Soltesz et al. | |
| 2006/0264772 A1 | 11/2006 | Aljuri et al. | |
| 2007/0005083 A1 | 1/2007 | Sabanathan et al. | |
| 2007/0096048 A1 | 5/2007 | Clerc | |

OTHER PUBLICATIONS

Von Euler and Liljestrand (1946) Observations on the Pulmonary Arterial Blood Pressure in the Cat, *Acta Physiol. Scand.* 12: 301-320.

* cited by examiner

*Primary Examiner* — Justine Yu
*Assistant Examiner* — Latoya M Louis
(74) *Attorney, Agent, or Firm* — Wilson Sonsini Goodrich & Rosati

(57) ABSTRACT

Lung conditions are treated by implanting a flow restrictor in a passageway upstream from a diseased lung segment. The restrictor will create an orifice at the implantation site which inhibits air exchange with the segment to induce controlled atelectasis and/or hypoxia. Controlled atelectasis can induce collapse of the diseased segment with a reduced risk of pneumothorax. Hypoxia can promote gas exchange with non-isolated, healthy regions of the lung even in the absence of lung collapse.

26 Claims, 15 Drawing Sheets

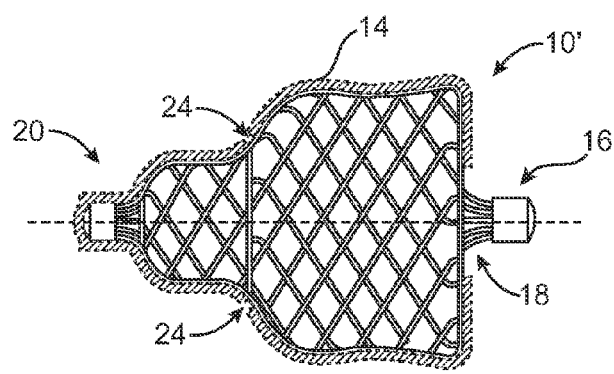
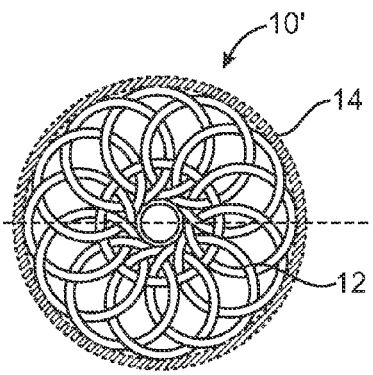
FIG. 2A  FIG. 2B
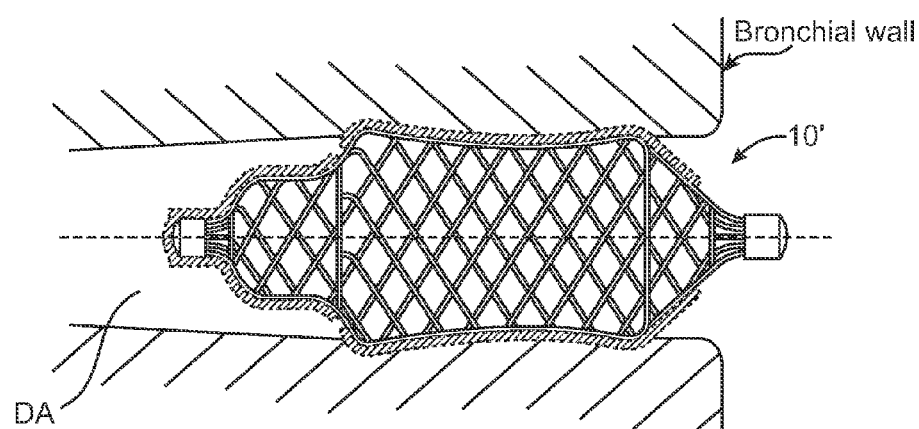
FIG. 2C
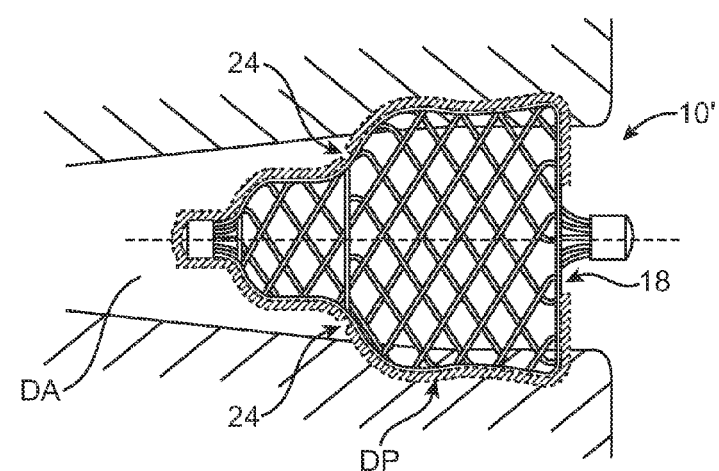
FIG. 2D

METHODS AND DEVICES TO INDUCE CONTROLLED ATELECTASIS AND HYPOXIC PULMONARY VASOCONSTRICTION

CROSS-REFERENCES TO RELATED APPLICATIONS

The present application claims the benefit of provisional U.S. Application No. 60/780,577, filed Mar. 8, 2006, the full disclosure of which is incorporated herein by reference.

BACKGROUND OF THE INVENTION

1. Field of the Invention

The present invention relates generally to medical methods, systems, and kits. More particularly, the present invention relates to methods and apparatus for the treatment of lung diseases, such as COPD, by creating and controlling atelectasis and hypoxia in segments of lung tissue.

Chronic obstructive pulmonary disease (COPD) is a significant medical problem affecting sixteen million people or about 6% of the U.S. population. Specific diseases in this group include chronic bronchitis, asthmatic bronchitis, and emphysema. While a number of therapeutic interventions are used and have been proposed, none are completely effective, and COPD remains the fourth most common cause of death in the United States. Thus, improved and alternative treatments and therapies would be of significant benefit.

Management of COPD is largely medical and infrequently surgical. Initially, exercise and smoking cessation are encouraged. Medications including bronchodilators and anti-inflammatories are routinely prescribed. Pulmonary rehabilitation has been shown to improve quality of life and sense of well being. Long term oxygen is generally reserved for the more severely affected patients.

Emphysema is a condition of the lung characterized by the abnormal permanent enlargement of the airspaces distal to the terminal bronchiole, accompanied by the destruction of their walls. It is known that emphysema and other pulmonary diseases reduce the ability of part of the lungs to fully expel air during the exhalation phase of the breathing cycle. During breathing, the diseased portion of the lung does not fully recoil due to the diseased lung tissue being less elastic than healthy tissue. Consequently, as the airways normally held open by the elastic pull of the lungs become floppy and the diseased lung tissue exerts a diminished driving force during exhalation, the airways close prematurely resulting in air trapping and hyperinflation.

In addition, hyper-expanded lung tissue occupies more of the pleural space than healthy lung tissue. In most cases, only a part of the lung is diseased while the remaining portion is relatively healthy and therefore still able to efficiently carry out oxygen exchange. By taking up more of the pleural space, the hyper-expanded lung tissue reduces the space available to accommodate the healthy, functioning lung tissue. As a result, the hyper-expanded lung tissue causes inefficient breathing by compressing the adjacent functional airways, alveolar units, and capillaries in relatively healthier lung tissue.

Lung function in patients suffering from some forms of COPD can be improved by reducing the effective lung volume, typically by resecting diseased portions of the lung. Resection of diseased portions of the lungs both promotes expansion of the non-diseased regions of the lung and decreases the portion of inhaled air which goes into the lungs but is unable to transfer oxygen to the blood. Accordingly, recruitment of previously compressed functional airways, alveolar units, and capillaries in relatively healthier lung is possible resulting in more gas exchange in addition to better matching of lung and chest wall dimensions. Lung reduction is conventionally performed in open chest or thoracoscopic procedures where the lung is resected, typically using stapling devices having integral cutting blades.

While effective in many cases, conventional lung volume reduction surgery (LVRS) is significantly traumatic to the patient, even when thoracoscopic procedures are employed. Such procedures often result in the unintentional removal of healthy lung tissue, and frequently leave perforations or other discontinuities in the lung which result in air leakage from the remaining lung. Even technically successful procedures can cause respiratory failure, pneumonia, and death. In addition, many older or compromised patients are not able to be candidates for these procedures.

As an alternative to LVRS, endobronchial volume reduction (EVR) uses endobronchially introduced devices which plug or otherwise isolate a diseased compartment from healthier regions of the lung in order to achieve volume reduction of the diseased compartment. Isolation devices may be implanted in the main airways feeding the diseased region of the lung, and volume reduction takes place via absorption atelectasis after implantation or via collapse by actively suctioning of the target compartment prior to implantation. These implanted isolation devices can be, for example, one-way valves that allow flow in the exhalation direction only or occlusive devices that prevent flow in both directions.

While a significant improvement over LVRS, EVR suffers from a significant risk of pneumothorax. Pneumothorax is a condition which results from air entering the pleural space surrounding the lung. For reasons that are not fully understood, it has been found by the inventors herein that a sudden blockage of a feeding bronchus can create conditions in the isolated lung region which can in some cases cause a pneumothorax. A spontaneous pneumothorax can result from the tearing of pleural adhesions and blebs lying under the visceral pleura of the non-treated lung areas during the rapid development of absorption atelectasis in the treated lung area.

For these reasons, it would be desirable to provide alternative and improved methods and devices for performing endobronchial volume reduction and other lung therapies where the risk of inducing a pneumothorax is reduced or eliminated.

2. Description of the Background Art

U.S. Pat. No. 6,679,264 describes an exemplary flow control element that limits, but does not block, fluid flow in at least one direction. The flow control element comprises a valve member supported by a ring. The valve member is preferably a duckbill-type valve having a similar construction to that of the valve member, except that the flaps are formed, secured, oriented or otherwise configured to maintain a flow opening when in their flow-controlling (as opposed to flow-allowing) orientation. The opening is sized and configured to achieve desired flow characteristics through the flow control element.

U.S. Pat. No. 6,722,360 describes devices and methods for improving breathing in patients with COPD. A mouthpiece is provided, or a device is implanted in the trachea or bronchial passage, to selectively increase flow resistance to expiration while minimally increasing flow resistance to inspiration. The methods and apparatus rely on increasing proximal flow resistance in a manner which mimics "pursed lip" breathing during exhalation which has been found to benefit patients suffering from this disease by keeping the distal airways open for a longer period of time and allowing more of the inspired air volume to be evacuated during the longer exhalation time.

U.S. Pat. No. 7,011,094 describes devices and methods for implanting sealing components within bronchial lumens. The sealing components may include a septum which can be penetrated with a dilation device which can provide a valve or open flow path through the septum.

U.S. 2007/0005083 describes the treatment of diseased lung segments by placing a blocking element in an airway of the lung which leads to the diseased segment.

BRIEF SUMMARY OF THE INVENTION

In accordance with the present invention, the inventors herein have discovered that diseased regions of the lung may be treated by restricting the exchange of air through an airway or bronchus which feeds the diseased region. In contrast to the endobronchial volume reduction (EVR) protocols where air flow from the diseased region into the feeding airway or bronchus is blocked (typically by a one-way valve or a fully occlusive element), the present invention relies on reducing the rate of air exchange between the diseased region and the feeding airway or bronchus while allowing a reduced rate of air flow in both the inhalation or inspiratory direction and the exhalation or expiratory direction.

Typically, the restriction will be provided by a restrictor which is implanted in the feeding airway or bronchus. The restrictor may be an orifice, a small diameter tube, a perforated membrane, a densely braided structure, perimeter channels, or other fixed-resistance element that impedes the flow of air equally in both directions. Alternatively, the resistor could provide a differential resistance in the two flow directions, for example including two or more parallel flow paths where some of the flow paths are blocked in the inhalation or exhalation direction (but at least some flow paths remain available to permit bi-directional flow at all times). Still further alternatively, the flow resistor could have a variable resistance, e.g., being an iris or other variable resistance valve element. In all cases, however, the flow resistor will permit air flow, usually being about equal, in both the inhalation and exhalation directions to provide for a controlled atelectasis, an induced hypoxia, or in some cases elements of both atelectasis and hypoxia.

In a first aspect of the present invention, the reduced exchange of air between the feeding airway or bronchus and the diseased or other targeted region of the lung to be treated will induce a controlled atelectasis. "Atelectasis" is the collapse of part or all of the lung region as a result of the reduction of air flow into the region and absorption of the remaining air volume. The air which is in the targeted region will be absorbed by the pulmonary blood circulation over time. Typically, the rate of absorption is small compared to the rate at which the targeted region is filled with new air and large amounts of air come and go with a residual portion of it always remaining in the targeted lung region. By fully blocking the flow of air into the targeted lung region, as is the case with prior EVR protocols, the entrance of new air into the targeted lung region stops abruptly, and absorption of the residual air volume takes place more rapidly. Consequently, the collapse of the treated region can be uncontrolled and occur too rapidly, presenting a significant risk of pneumothorax, which is the collection of air or gas in the space surrounding the lung. By providing the controlled (but restricted) exchange of air between the treated lung region and the feeding airway or bronchus, the collapse of the treated lung region will occur more gradually and reduce the risk of pneumothorax. Gas exchange between the treated lung region and the feeding airway will decrease gradually over time until the pressure difference across the restrictor element reaches zero.

At that time, atelectasis has fully developed and absorption ceases. That is, the treated region will eventually collapse as with the EVR protocols, but at a slower rate with the reduced risk of pneumothorax. Typically, the collapse of the treated lung region via atelectasis when treated by the flow restriction methods of the present invention will occur when there is little or no collateral ventilation of the treated lung region.

In a second aspect of the present invention, the reduced exchange of air between the treated lung region and the feeding airway or bronchus will result in hypoxic pulmonary vasoconstriction (HPV), referred to hereinbelow as "hypoxia." Hypoxic pulmonary vasoconstriction as a result of asphyxia has been observed since the beginning of the twentieth century, with the first convincing evidence of its existence reported by von Euler and Liljestrand in 1946 (Von Euler and Liljestrand (1946) Observations on the Pulmonary Arterial Blood Pressure in the Cat, *Acta Physiol. Scand.* 12: 301-320). Hypoxic pulmonary vasoconstriction shifts blood flow from the hypoxic lung regions to adjacent lung regions which are not hypoxic or are less hypoxic. Thus an induced hypoxic condition in a diseased lung segment can shift blood flow to other healthier lung regions to improve gas exchange and arterial oxygenation.

According to the present invention, there is a potentially significant benefit for a patient who undergoes a simple procedure that creates localized hypoxia in the lung, even with lessened or no lung volume reduction which can occur if, for example, the treated region is collaterally ventilated. By implanting a flow restrictor in the main airway feeding a region of the lung targeted for treatment, a reduction in ventilation to the restricted region takes place. Consequently, a localized hypoxic pulmonary vasoconstriction is induced which diverts blood flow away from the induced hypoxic region to other areas in the lung which are more adequately ventilated and better perfused. As a result, ventilation and perfusion are better matched and the potential for gas exchange is increased.

According to the methods of the present invention, a lung condition may be treated by implanting an air flow restrictor in an airway of a patient's lung. The restrictor reduces air flow exchange between upstream of the restrictor and downstream of the restrictor. Such air flow restriction induces at least one of controlled atelectasis and localized hypoxia in the treated region beyond the restriction. Controlled atelectasis will cause collapse of the treated region downstream of the air flow restrictor, occurring typically in treated lung regions having minimal or no collateral ventilation with adjacent lung regions. The rate of air exchange between the treated lung region and the feeding airway or bronchus will be controlled to permit collapse of the treated lung region over a preselected time period, usually in the range from 12 hours to 30 days, preferably in the range from 3 days to 15 days. Particular restrictors having dimensions and characteristics to provide for such a controlled collapse are described in more detail below.

Localized hypoxia will typically occur without significant collapse of the treated lung region, wherein the hypoxia shifts blood flow away from the treated region and to other, typically more healthy, regions of the lung where improved blood oxygenation may occur. Such localized hypoxia will typically occur in treated lung regions which have significant collateral flow with adjacent lung regions, where the collateral flow will typically inhibit or prevent atelectasis and collapse.

The air flow restrictors of the present invention will typically reduce the volumetric rate of the air flow exchange by an amount in the range from 10% to 99.99% of the unrestricted volumetric rate of air flow exchange, typically in the range from 99% to 99.9% of such unrestricted volumetric air flow.

The restrictors useful in the methods of the present invention will comprise at least one open passage or flow path which permits restricted air flow exchange. In some instances, the restrictors may consist of a single orifice, while in other instances the restrictors may include a plurality of passages, such as a plurality of openings or perforations formed in a membrane or other blocking element. Usually, the open passage area in the flow restrictor will be in the range from 0.01% to 90% of the total cross-sectional area of the restrictor when implanted in the airway, more typically being in the range from 0.1% to 1% of said area. The total passage area will typically be in the range from 0.01 mm$^2$ to 5 mm$^2$, more typically from 0.1 mm$^2$ to 1 mm$^2$.

In a further aspect of the present invention, a bronchial flow restrictor comprises a body having at least one open passage or flow path to permit bidirectional air flow therethrough. The body will be adapted to be expanded and anchored within the lung airway for the control of air exchange with a downstream region of the lung. The passage may consist of a single passage, e.g., in the case of an orifice plate, or the restrictor may include a plurality of passages, e.g., in the case of a perforate plate, membrane, or the like. Typically, the open passage area of the restrictor will be in the range from 0.01% to 90% of the cross-sectional area of the body when expanded. Usually, the total area of the open passages will be in the range from 0.01 mm$^2$ to 50 mm$^2$, typically from 0.1 mm$^2$ to 1 mm$^2$. In alternative embodiments, the passages may be formed on the outside of the body. Typically, the body will be elastic so that it may be constrained to a smaller width for introduction to the lung airway and then released to self-expand and anchor at a target location within the airway. Alternatively, the flow restrictor may be malleable (capable of non-elastic expansion) and be expandable by the application of an internal expansion force, e.g., using a deployment balloon.

In a specific embodiment, the flow restrictor comprises a collapsible medical device made of a plurality of strands or ribbons that are braided, woven, or otherwise enmeshed into a cylindrical shape having a proximal end and a distal end. The strands are connected by a clamping member or otherwise to permit radial expansion and contraction as the axial length is shortened or extended. The braided structure may be very populated with the wire strands or ribbons so that a generally contiguous surface is formed, where the surface has numerous openings or apertures formed between the intersections of adjacent strands or ribbons. The openings provide an equal restriction to air flows going in and out of the target lung segments. The strands may be bare-metal wires, polymer wires or metal wires laminated with a polymer. Optionally, the braided structure may be coated with an eluting drug such as an antibiotic or one for the purpose of reducing or eliminating granulation tissue growth to facilitate elective removal of the restrictor if desired. In another embodiment, the braided structure is coated with a polymer material, but at certain locations it has one or more holes which create a restriction to air flows going in and out of the target lung segments. A variety of design options are presented by the accompanying drawings. This invention also relates to mucus transporting means to be provided with a flow restrictor. Such device would possess at its perimeters transport channels or ports for the physiological media.

BRIEF DESCRIPTION OF THE DRAWINGS

FIGS. 2A-2D illustrate a second embodiment of a flow restrictor constructed in accordance with the principles of the present invention, wherein flow apertures are located in a different location than illustrated in FIGS. 1A and 1B.

DETAILED DESCRIPTION OF THE INVENTION

In the descriptions below, specific designs for bronchial flow restrictors are described. The restrictors can be placed in any bronchial airway, but generally the airways between and including the lobar bronchus and sub-sub-segmental bronchi are the desired airways to restrict. The restrictor is intended to impede air flow in both the inspiratory and expiratory direction usually about equally, and either permanently or temporarily. Flow limitation can be from 10% to 99.99% reduction of flow, usually being from 99% to 99.9% of the unrestricted flow, depending on the clinical need.

The flow limitation will have at least one of two physiologic effects. In instances where the lung region distal to the restrictor is generally free from collateral ventilation, the restrictor will induce a controlled atelectasis. The distal lung region will collapse, although at a significantly slower rate of collapse than would be the case with complete occlusion of air flow into the region, and the risk of pneumothorax will be significantly reduced. In other instances where the lung region downstream from the flow restrictor is exposed to significant levels of collateral ventilation, the restricted air flow into and from the region will induce hypoxia. The resulting reduced oxygen concentrations distal to the restrictor will catalyze the von Euler reflex to shunt pulmonary perfusion to other, usually more healthy and functional, bronchopulmonary regions of the lung that have not been treated with a restrictor, and thus improve the ventilation-perfusion efficiency of the lung.

Figure 1A:
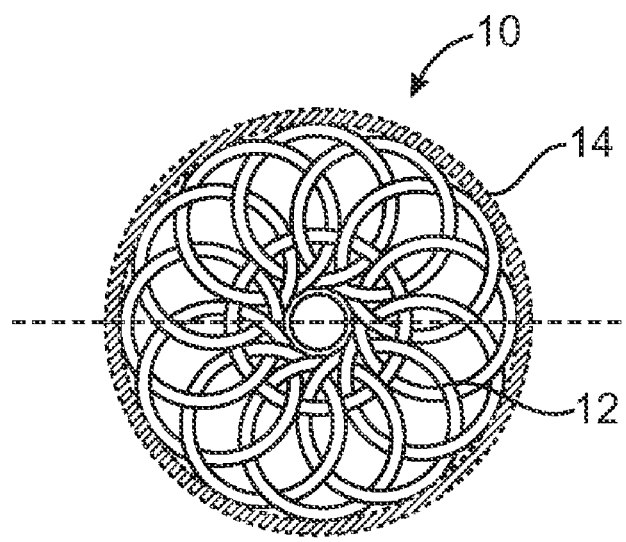
FIGS. 1A and 1B illustrate a first embodiment of a flow restrictor constructed in accordance with the principles of the present invention having flow apertures in a reduced diameter portion thereof.
Figure 1B:
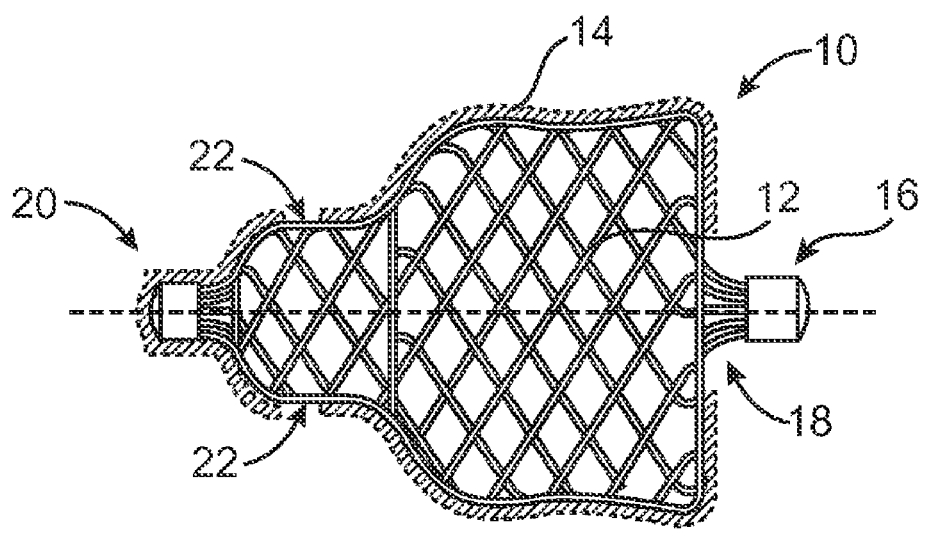

FIGS. 1A and 1B illustrate a bronchial flow restrictor (BFR) 10 constructed of an elastic wire frame 12 which is laminated with an elastomeric membrane 14. On the proximal end 16 of the BFR, the membrane 14 is incomplete or perforated, creating at least one vent hole 18. On the distal section 20 of the BFR, apertures 22 are formed in the membrane 14 to create a path for the gas flow. The size and shape of the vent hole 18 and apertures 22 can vary in order to provide a desired flow resistance within the range defined elsewhere herein. This general design permits collapsibility of the BFR for insertion into a small catheter for delivery into the lung, allowing self-expansion of the BFR when released from the catheter. The stepped configuration of this particular design allows the BFR to be placed at or near an airway bifurcation or airway narrowing. For example, the larger proximal end may be placed in a proximal airway so that the distal smaller section 20 extends into the next generation airway which is smaller because it is distal to the proximal airway. The flow restrictions can be fabricated by the techniques described for fabrication of fully occlusive elements and one-way valves set forth in U.S. Pat. No. 6,527,761 and commonly assigned, copending application Ser. No. 11/280,592, the full disclosures of which are incorporated herein by reference.

FIGS. 2A-2D describe a modified configuration 10' of the previously described BFR in which distal gas flow apertures 24 are positioned to be within the lumen of the distal airway DA after the BFR has been expanded from a radially constrained diameter in the airway to an unconstrained diameter which creates a dilated pocket DP (FIG. 2D) in the airway. Thus, the gas flow through apertures 24 is not obstructed by the bronchial wall.

Figure 3:
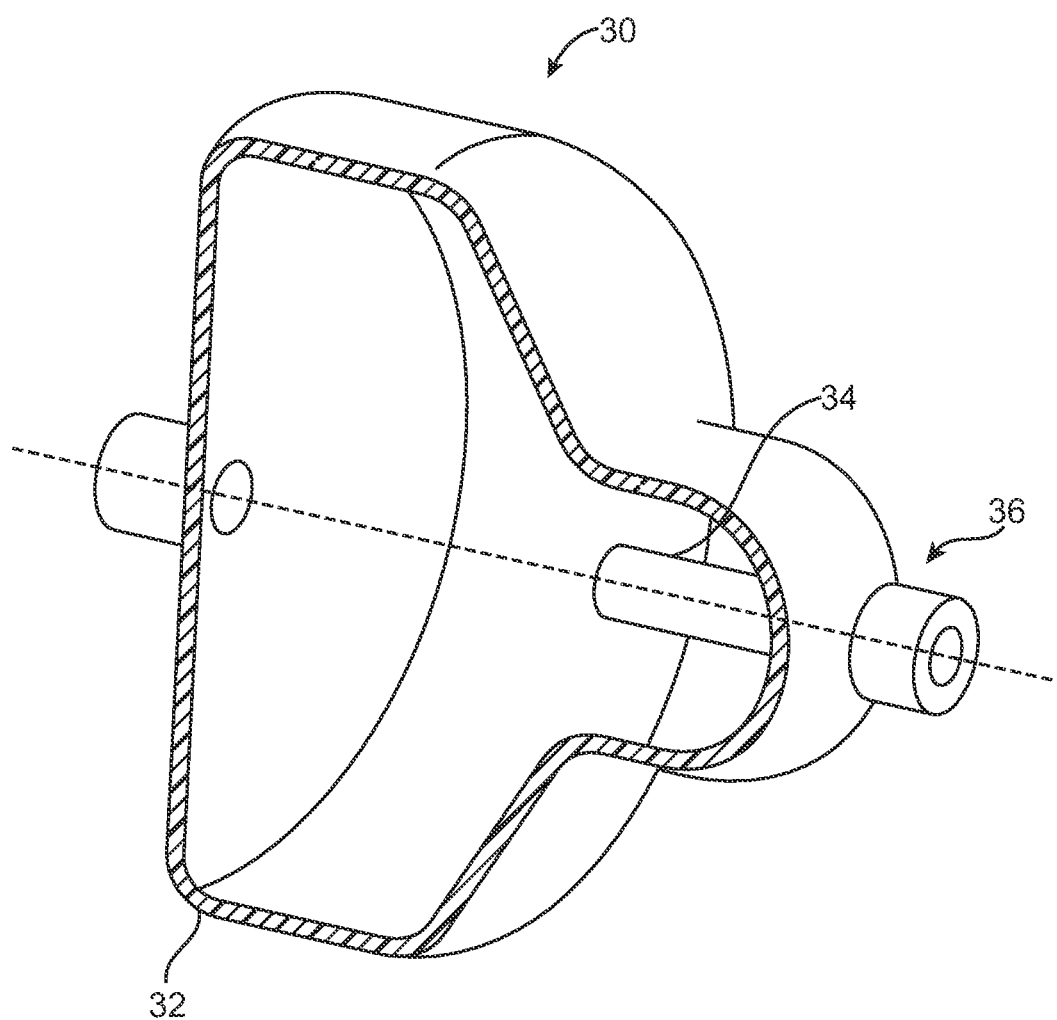
FIG. 3 illustrates a third embodiment of a flow restrictor comprising a silicone body having an orifice tube therein.

FIG. 3 is a cross-sectional view of BFR 30 in which a housing 32 includes a gas flow orifice tube 34 on its distal end 36. The housing can have a "uni-body" construction, typically being molded or cast from silicone or another biocompatible elastomer. In some instances, the housing 32 can have composite construction of wire frame with silicone membrane coating, or be formed from a variety of materials and construction methods. It can be collapsible and self expanding for a catheter based delivery. In other designs, the BFR can be malleable to allow plastic deformation and expansion by a balloon or other expandable deployment on the delivery catheter.

Figure 4:
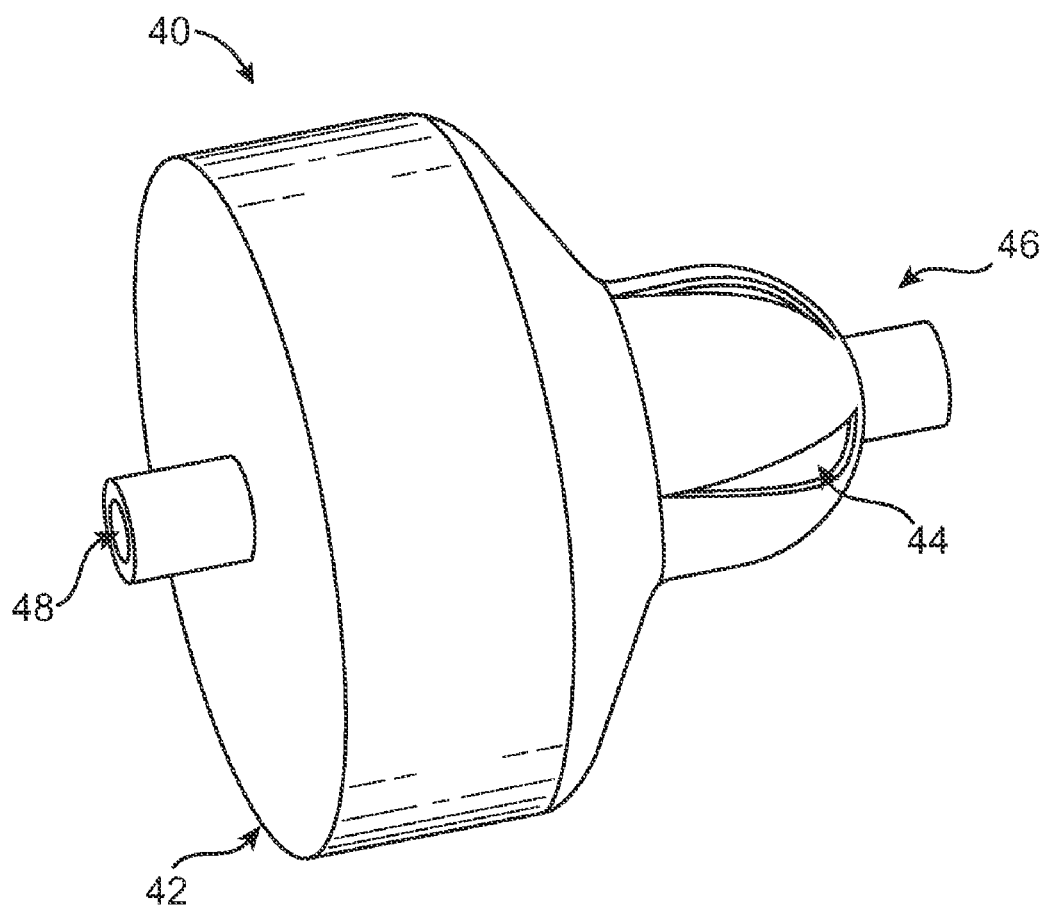
FIG. 4 illustrates a fourth embodiment of a flow restrictor constructed in accordance with the principles of the present invention, which comprises a continuous body structure having windows formed in one end thereof.

FIG. 4 illustrates a BFR 40 in which a housing 42 comprises a plurality of windows 44 in a wall of a distal section 46 in order to permit gas flow in and out of the housing. An orifice 48 at the opposite proximal end completes the gas flow path such that the device restricts but does not obstruct gas flow. As with previously described embodiments, the housing 42 can have a uni-body construction or comprise a wire frame with silicone or other membrane covering. It can be either collapsible and self expanding or balloon expandable.

Figure 5A:
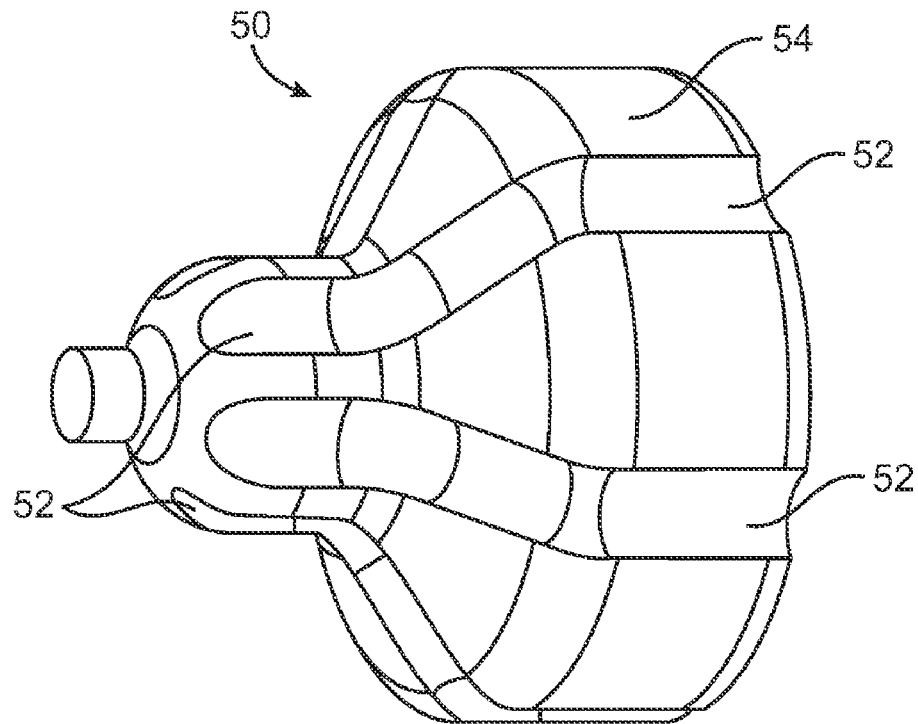
FIGS. 5A and 5B illustrate a fifth embodiment of a flow restrictor constructed in accordance with the principles of the present invention having flow channels formed in an outer surface thereof.
Figure 5B:
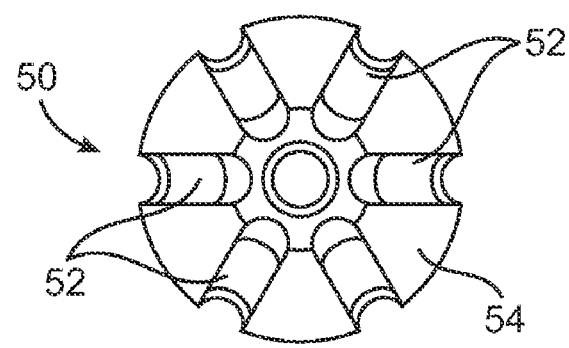

FIGS. 5A and 5B illustrate BFR 50 which has gas or fluid transport channels 52 shaped or formed into an outer surface or periphery of the housing body 54. The channels 52 will leave a space or gap between the airway wall in which the BFR is implanted and the surface of the BFR, thus providing a path for fluid flow in both directions. As mentioned previously, the housing 54 can have a uni-body or composite construction. The housing 54 can be collapsible and self expanding or balloon expandable.

Figure 6:
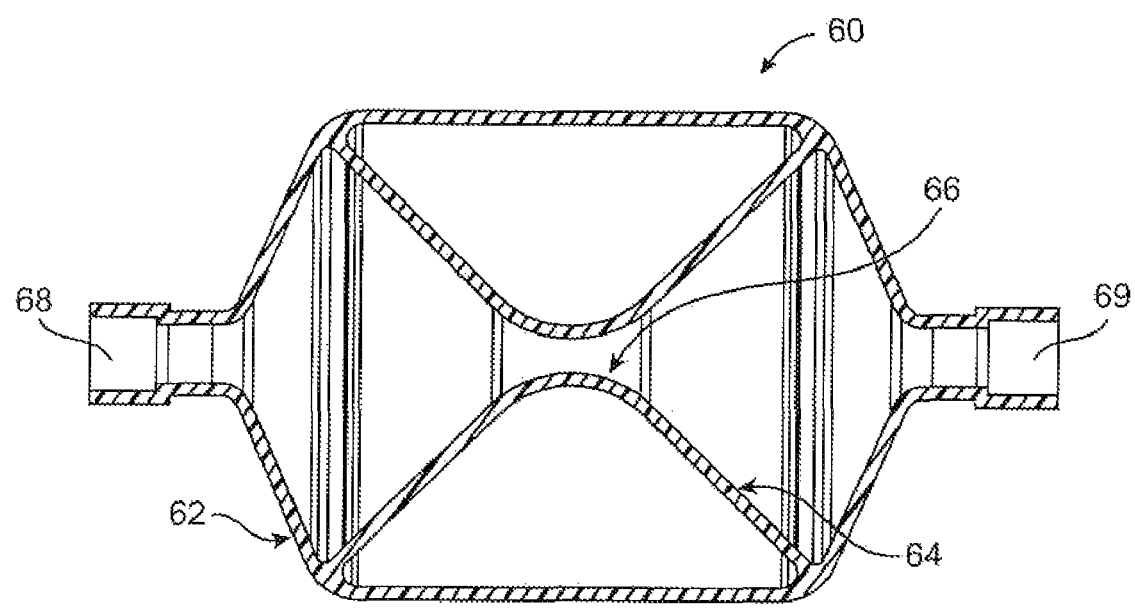
FIG. 6 illustrates a sixth embodiment of a flow restrictor constructed in accordance with the principles of the present invention having an internal tapered flow restrictive orifice.

FIG. 6 illustrates a BFR 60 in which a housing 62 houses a funnel-shaped (or hourglass-shaped) diaphragm 64 which provides a gas flow orifice 66 in the center of the diaphragm. Distal and proximal apertures 68 and 69, respectively, allow air flow into and out of the housing 62, and the tapered orifice 66 defined by the diaphragm 64 restricts the flow. The diameter of the orifice 66 can be selected to provide a desired flow resistance. The housing 62 can have a uni-body construction or be a wire braided structure encapsulated with silicone or other elastomere. The diaphragm can be a flexible silicone material or other elastomere in order to facilitate compressibility of the BFR 60 for insertion into the lung via a delivery catheter lumen.

Figure 7:
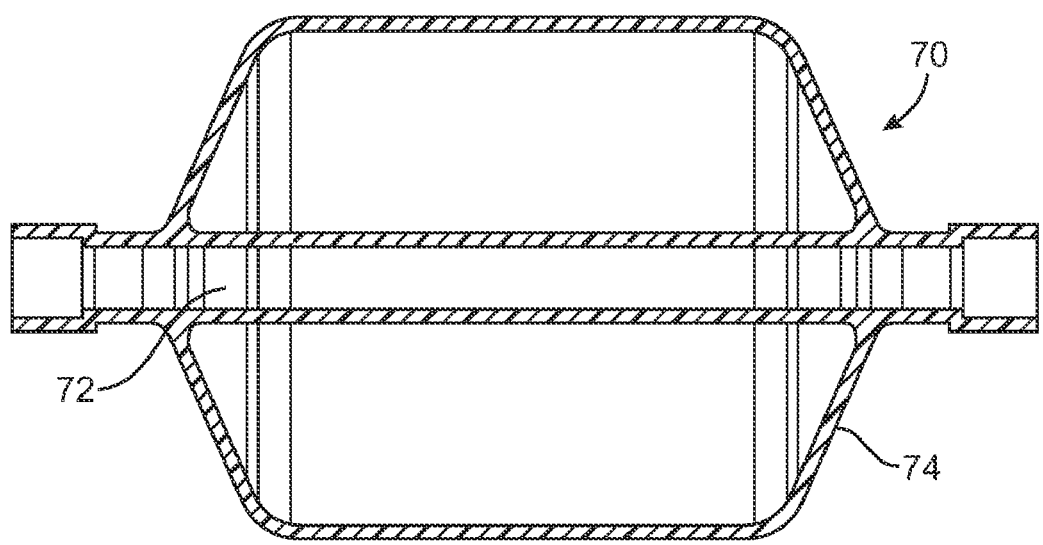
FIG. 7 illustrates a seventh embodiment of a flow restrictor constructed in accordance with the principles of the present invention having an internal tube which provides flow resistance.

FIG. 7 illustrates BFR 70 in which a gas flow tube 72 is axially aligned in a housing 74. Construction of the housing 74 can be similar to any of the concepts previously described. The gas flow tube 72 can be constructed of any tubular material, preferably being a flexible polymer. Flexibility is advantageous since a flexible tube will facilitate insertion into the lung. The housing 74 can have any of the constructions described previously.

Figure 8A:
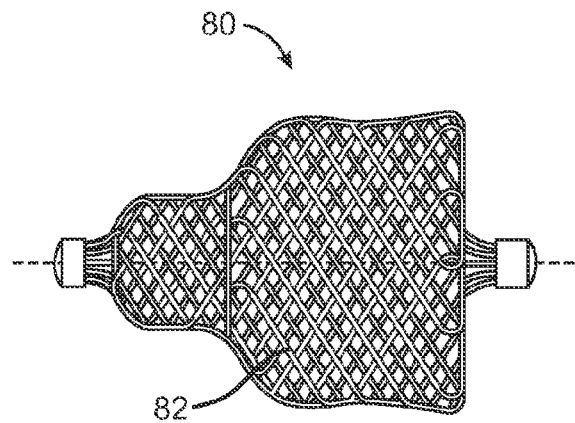
FIGS. 8A and 8B illustrate an eighth embodiment of a flow restrictor constructed in accordance with the principles of the present invention, wherein the flow restrictor has a bell shape and is constructed of a gas penetrable braid.
Figure 8B:
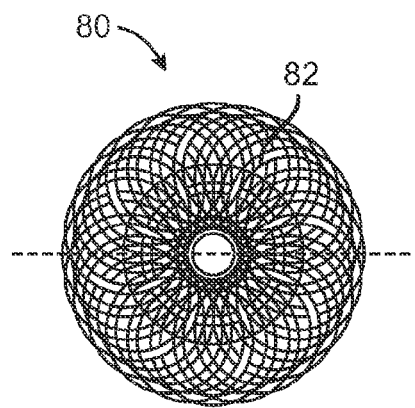
Figure 9A:
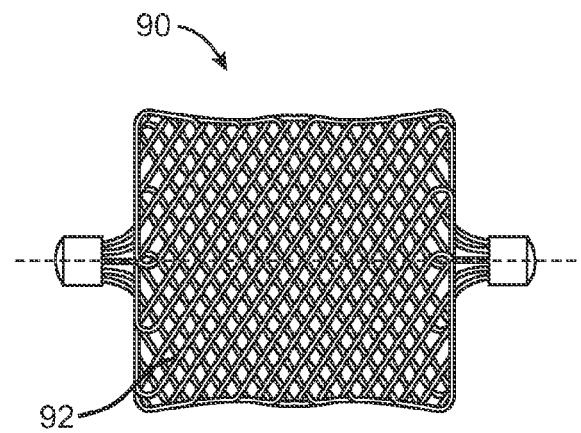
FIGS. 9A and 9B illustrate a ninth embodiment of a flow restrictor constructed in accordance with the principles of the present invention, wherein the flow restrictor comprises a cylindrical body formed of a gas penetrable braid.
Figure 9B:
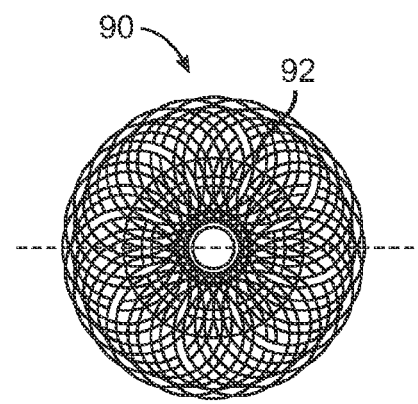

FIGS. 8A and B and 9A and B illustrate non-covered, tightly packed wire braid flow restrictors 80 and 90. The tight backing of the wire braid can eliminate the need for a membrane cover to achieve occlusion while providing a perforate or foraminous surface 82 and 92, respectively, to permit a controlled flow of air therethrough.

Figure 10:
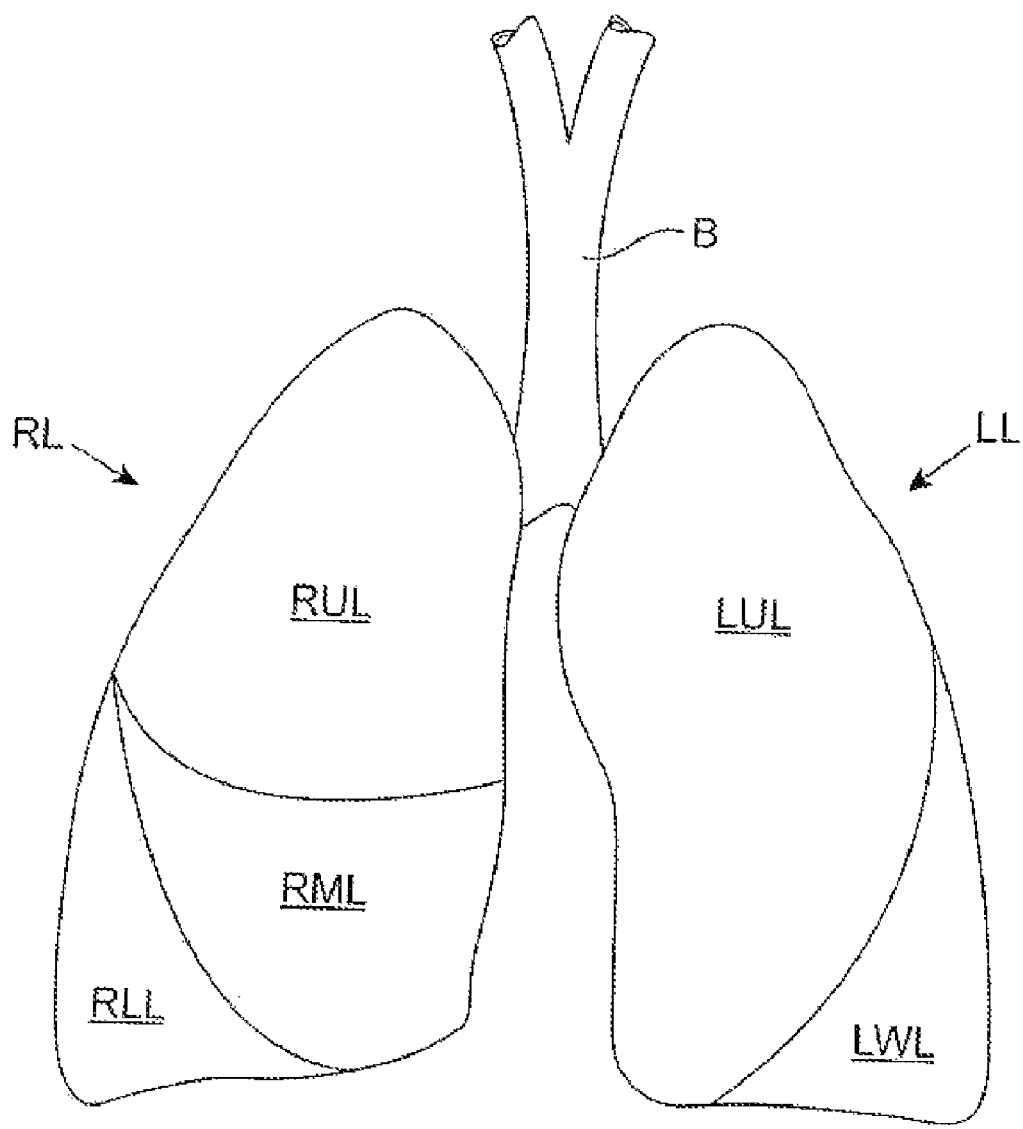
FIG. 10 is an anatomical diagram illustrating the lobar structure of the lungs of a patient.

Referring now to FIG. 10, the respiratory system of a patient starts at the mouth and extends through the vocal cords and into the trachea where it then joins the main stem bronchi B which leads into the right lung RL and the left lung LL. The bronchi going into the right lung divide into the three lobar bronchi which lead into the upper lobe RUL, the middle lobe RML and the lower lobe RLL. The lobes of the right lung include a total of ten segments (three in the RUL, two in the RML, and five in the RLL) which are discrete units of the lung separated from each other by a fibrous septum generally referred to as a lung wall. The left lung LL includes only an upper lobe LUL and a lower lobe LLL, where the individual lobes include four to five segments each Each lung segment, also referred to as a bronchopulmonary segment, is an anatomically distinct unit or compartment of the lung which is fed air by a tertiary bronchus and which oxygenates blood through a tertiary artery. Normally, the lung segment and its surrounding fibrous septum are intact units which can be surgically removed or separated from the remainder of the lung without interrupting the function of the surrounding lung segments. In some patients, however, the fibrous septum separating the lobes or segments may be perforate or broken, thus allowing air flow between the segments, referred to as "collateral ventilation."

Figure 11:
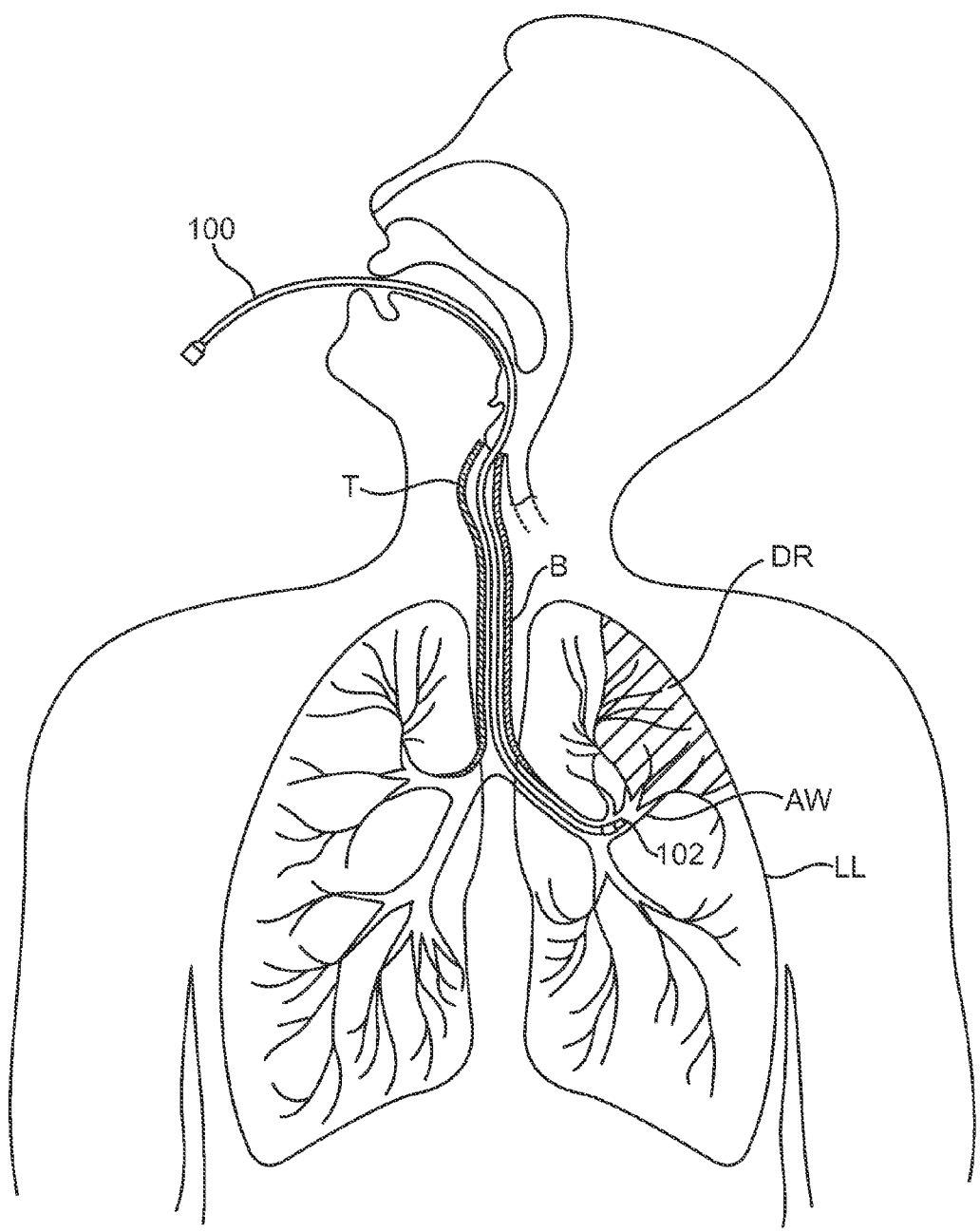
FIG. 11 illustrates the trans-esophageal endobronchial placement of a flow restrictor delivery catheter in an airway leading to a diseased lung region.
Figure 12:
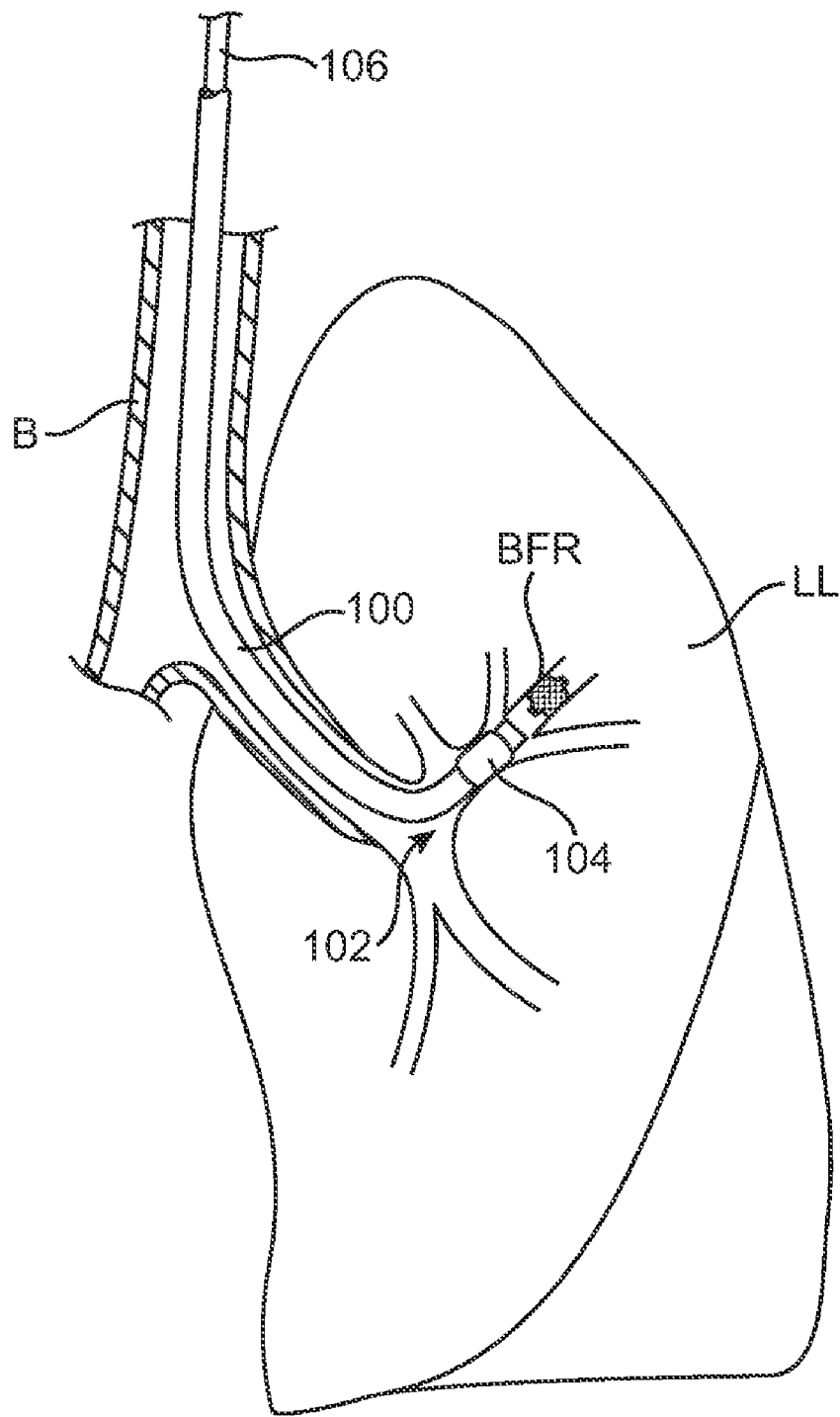
FIG. 12 illustrates placement of a flow restrictor by the catheter placement device of FIG. 11.

Use of a delivery catheter 100 for placement of a BFR in accordance with the principles of the present invention is shown generally in FIGS. 11 and 12. The catheter 100 is advanced through the mouth, down through the trachea T, and through the main bronchus into the left lung LL. A distal end 102 of catheter 100 is advanced into the left lung LL, and further advanced to an airway AW which feed a diseased lung region DR. The catheter 100 may be introduced through the main bronchus B and into the left lung LL without the use of a bronchoscope or other primary introducing catheter, as illustrated in FIG. 11. Alternatively, the catheter 100 may be introduced through a conventional bronchoscope (not shown) which is positioned in the main bronchus above the branch between the right and left lungs. Alternatively, the catheter 100 may be introduced into the lung through a scope, such as a visualizing endotracheal tube (not shown) which is capable of advancing into the branching airways of the lung is advantageous in that it facilitates positioning of the delivery catheter 100 at the desired airway leading to a target lung segment. Construction and use of a visualizing endotracheal tube is taught, for example, in U.S. Pat. No. 5,285,778, the full disclosure of which is incorporated herein by reference. It would be possible, of course, to utilize both the bronchoscope and the endotracheal tube in combination for positioning the delivery catheter 100 in the desired lung segment airway.

After the distal end 102 of the delivery catheter 100 has been positioned in the main airway or bronchus feeding the diseased region DR, the catheter can optionally be immobilized, for example by inflating a balloon or cuff 104. After immobilizing the distal end of the catheter, a pusher or other element 106 can be advanced in order to eject the bronchial flow restrictor BFR in the bronchus, where it optionally self-expands to anchor in place. Although not illustrated, it would also be possible to use an inflatable balloon or other deployment device on the catheter 100 in order to position a plastically deformable restrictor at a desired location.

Figure 13A:
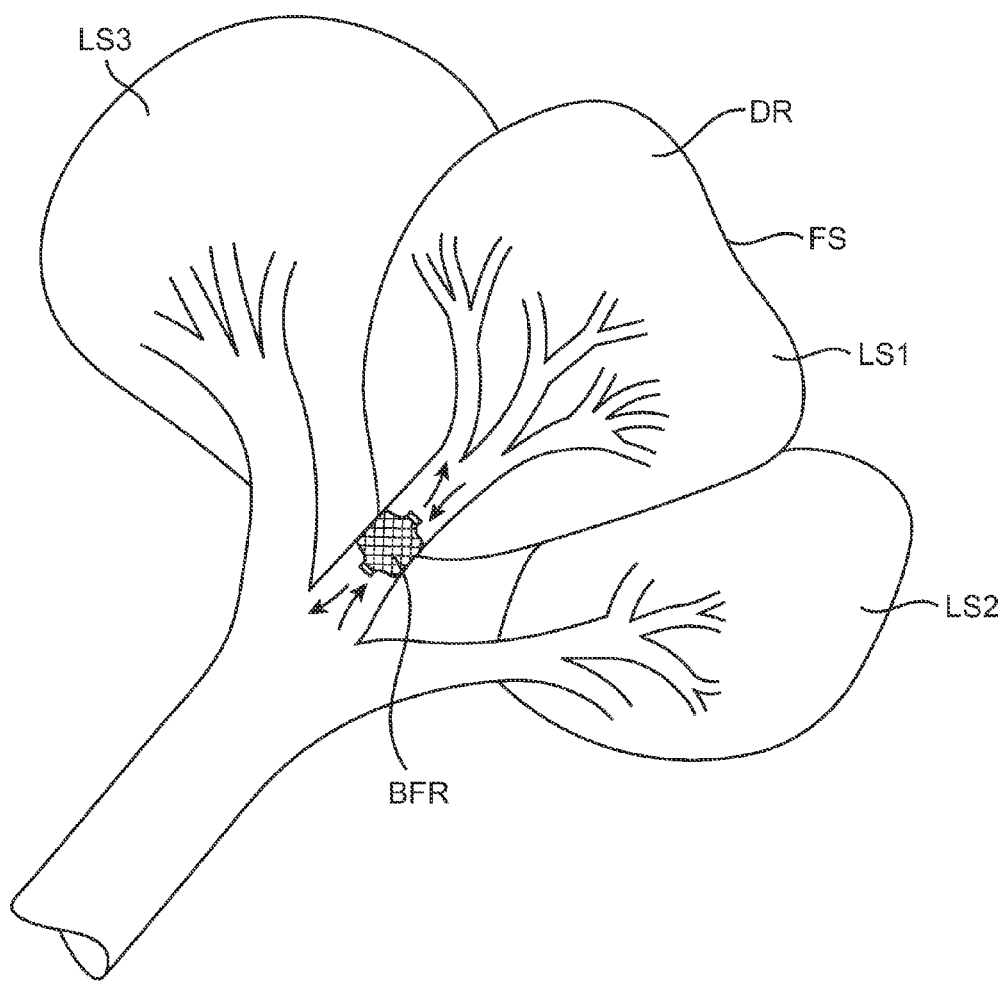
FIGS. 13A and 13B illustrate the physiologic effect of placement of the flow restrictor at an airway leading to a diseased lung region with little or no collateral ventilation.
Figure 13B:
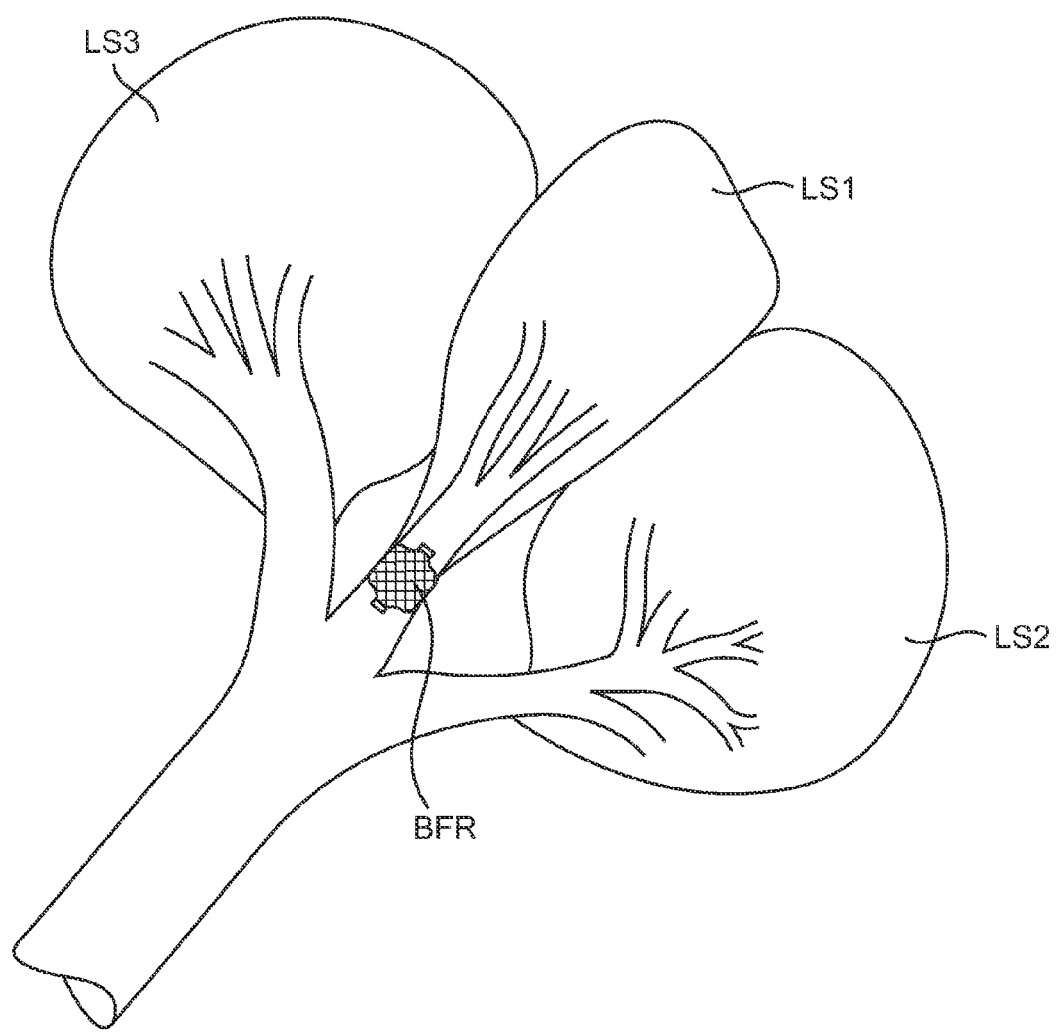

Referring now to FIGS. 13A and 13B, after the bronchial flow restrictor BFR has been placed in the airway leading to a diseased region DR, illustrated as a first lung segment LS1, air flow into and out of the segment as the patient inhales and exhales will be restricted by placement of the BFR, as generally described above. As shown in FIGS. 13A and 13B, the first lung segment LS1 is surrounded by a fibrous septum FS which is generally intact so that little or no collateral ventilation with adjacent lung segments LS2 and LS3 will occur. Thus, as shown in FIG. 13B, the reduced air flow into and out of the treated lung segment LS1 will induce atelectasis and cause the treated segment to deflate. Deflation of the treated segment LS1, in turn, allows the adjacent, healthier lung segments LS2 and LS3 to expand and provide improved patient blood oxygenation. Moreover, the slower rate of atelectasis reduces the risk to the patient of pneumothorax, as discussed above.

Figure 14A:
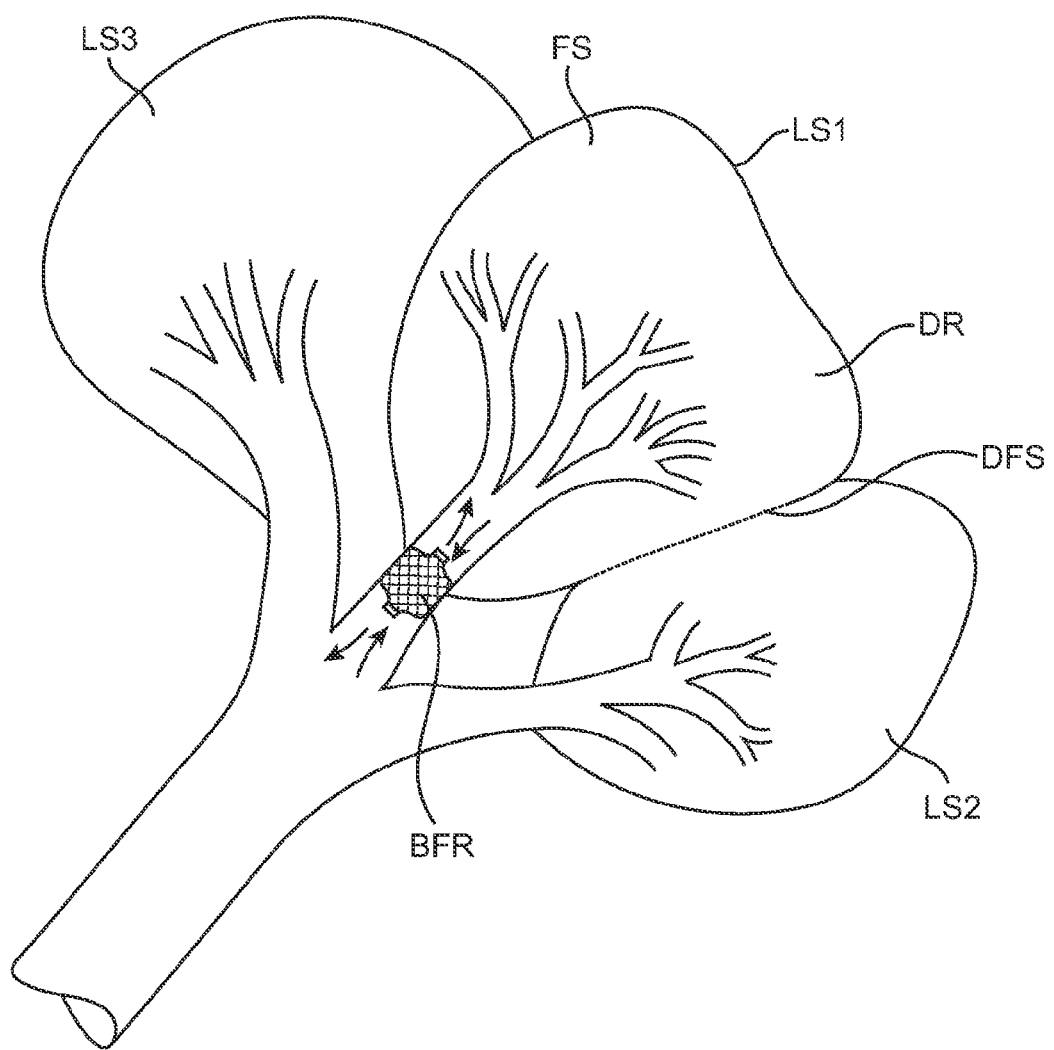
FIGS. 14A and 14B illustrate the physiologic response induced by placement of a flow restrictor at an airway feeding a diseased lung region which has significant collateral ventilation.
Figure 14B:
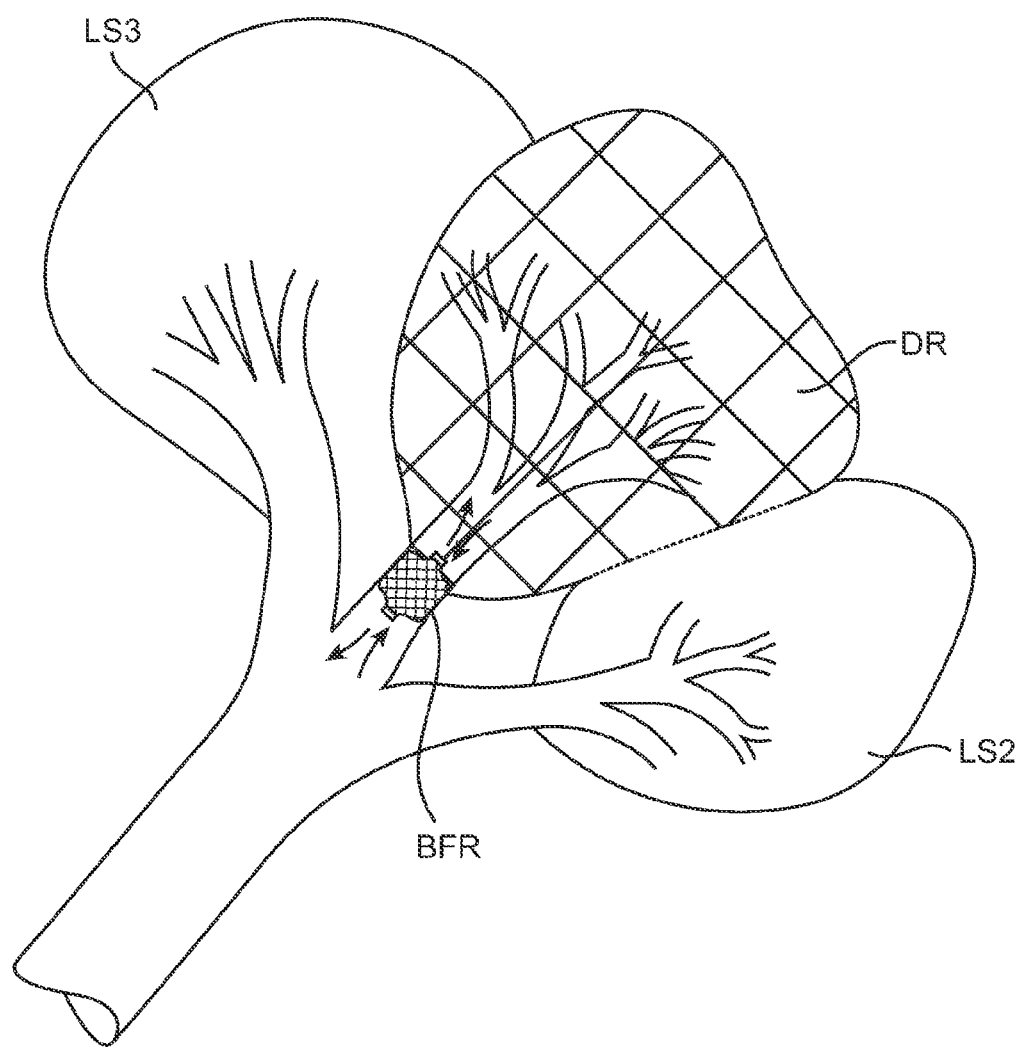

Referring now to FIGS. 14A and 14B, in other instances, the diseased lung region DR may have a perforated or otherwise damaged region of the fibrous septum DFS which permits collateral ventilation between the diseased region (LS1) and an adjacent lung region LS2. In those instances, air entering via the collateral channels is already low in oxygen and placement of the bronchial flow restrictor BFR will significantly reduce the amount of oxygenated air entering the diseased region LS1/DR via the feeding bronchus. As shown in FIG. 14B, over time, the reduced and non-oxygenated air exchange with the diseased region DR will induce hypoxia in the region (shown with the cross-hatching) which will catalyze the von Euler reflex to shunt pulmonary perfusion to other healthier regions of the lung, such as adjacent healthy segments LS2 and LS3.

It will be appreciated, however, that the induced lung collapse and induced hypoxia may occur to differing degrees in even the same treated region. In particular, the shift between lung collapse and hypoxia may depend, at least in part, on the degree to which collateral ventilation exists between the diseased region and adjacent healthier lung regions. Thus, although it may be desirable to perform a diagnostic on the patient to determine whether or not a particular diseased region is subject to collateral ventilation (as taught, for example, in commonly owned, copending application Ser. No. 11/296,951, filed on Dec. 7, 2005, the full disclosure of which is incorporated herein by reference), it would not be necessary. Treatment of diseased lung regions using the bronchial flow restrictors of the present invention may be advantageous regardless of the collateral ventilation status of a particular region.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating a lung condition, said method comprising: implanting an air flow restrictor in an airway of the lung, wherein said restrictor allows a reduced bidirectional volumetric rate of air flow exchange between upstream of the restrictor and downstream of the restrictor through a tube that is integral to the restrictor, wherein the bidirectional volumetric rate of air flow is equal in both directions and wherein such air flow rate reduction induces at least one of controlled atelectasis and localized hypoxia in a treated region of the lung downstream of the restrictor.

2. A method as in claim 1, wherein controlled atelectasis is induced which causes collapse of the treated region downstream of the air flow restrictor.

3. A method as in claim 2, wherein the treated region collapses over a period in the range from 12 hours to 30 days.

4. A method as in claim 1, wherein localized hypoxia is induced without collapse of the treated region, wherein the hypoxia shifts blood flow away from the treated region to other regions of the lung.

5. A method as in claim 4, wherein the treated region has collateral flow channels with adjacent lung regions, wherein collateral flow channels inhibit atelectasis and collapse.

6. A method as in claim 1, wherein the volumetric rate of air flow exchange is reduced by a percentage from 10% to 99.99% relative to an unrestricted volumetric rate of air flow exchange.

7. A method as in claim 6, wherein the percentage is from 99% to 99.9%.

8. A method as in claim 1, wherein the passage permits air flow exchange.

9. A method as in claim 8, wherein the passage consists of a single orifice.

10. A method as in claim 8, wherein the restrictor includes a plurality of passages.

11. A method as in claim 8, wherein the open passage area is in the range from 0.01% to 90% of the area of the airway where the restrictor is implanted.

12. A method as in claim 8, wherein the open passage area is in the range from 0.01 mm squared to 50 mm squared.

13. A method as in claim 1, wherein implanting comprises releasing a self-expanding restrictor from a constraint so that the restrictor opens and anchors in the airway.

14. A method as in claim 13, wherein the restrictor is released from a tubular introducer.

15. A method as in claim 1, wherein the restrictor is expanded by an expansion member.

16. A bronchial flow restrictor comprising a body having a continuously and constantly open tube that is integral to the body to permit equal bidirectional volumetric rate of air flow therethrough, wherein the body is adapted to be expanded and anchored within a lung airway for the control of air exchange with a downstream region of the lung, wherein the passage has dimensions selected to provide a reduced bidirectional volumetric flow rate which induces at least one of controlled atelectasis and localized hypoxia in a treated region beyond an anchored location in the airway.

17. A bronchial flow restrictor as in claim 16, wherein the passage consists of a single orifice.

18. A bronchial flow restrictor as in claim 16, wherein the restrictor includes a plurality of passages.

19. A bronchial flow restrictor as in claim 16, wherein the open passage area is in the range from 0.01% to 90% of the cross-sectional area of the body when expanded.

20. A bronchial flow restrictor as in claim 16, wherein the open passage area is in the range from 0.01 mm squared to 50 mm squared.

21. A bronchial flow restrictor as in claim 16, wherein the at least one passage comprises a plurality of channels on the outside of the body.

22. A bronchial flow restrictor as in claim 16, wherein the body is elastic so that it can be constrained to a smaller width for introduction to the lung airway and released to self-expand and anchor at a designated location.

23. A bronchial flow restrictor as in claim 16, wherein the body is malleable and expandable by application of an expansion force.

24. A bronchial flow restrictor as in claim 16, wherein the body comprises a plurality of woven elements adapted to radially self-expand and form a generally contiguous surface having a plurality of openings which provide a resistance to the bi-directional flow of air when deployed in an airway of a lung.

25. A system comprising: a bronchial flow restrictor having a body having a continuously and constantly open tube that is integral to the body to permit equal, reduced, bidirectional volumetric rate of air flow therethrough, wherein the body is adapted to be expanded and anchored within a lung airway for the control of air exchange with a downstream region of the lung; and a delivery catheter adapted to deliver the bronchial flow restrictor in an airway of the lung.

26. A system as in claim 25, wherein the delivery catheter comprises an outer catheter tube and an inner pusher member, wherein the bronchial flow restrictor is receivable in a distal end of the outer catheter tube and the inner pusher member is adapted to advance and release the bronchial flow restrictor from the tube.

* * * * *